US010408760B2

(12) United States Patent
Wang et al.

(10) Patent No.: US 10,408,760 B2
(45) Date of Patent: Sep. 10, 2019

(54) RAMAN SPECTRUM DETECTING METHOD FOR ELIMINATING PACKAGE INTERFERENCE AND ELECTRONIC DEVICE THEREOF

(71) Applicant: Nuctech Company Limited, Beijing (CN)

(72) Inventors: Hongqiu Wang, Beijing (CN); Wei Gou, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 15/835,306

(22) Filed: Dec. 7, 2017

(65) Prior Publication Data
US 2018/0164216 A1    Jun. 14, 2018

(30) Foreign Application Priority Data
Dec. 8, 2016  (CN) .......................... 2016 1 1127731

(51) Int. Cl.
*G01J 3/44*    (2006.01)
*G01N 21/65*    (2006.01)
(Continued)

(52) U.S. Cl.
CPC ................ *G01N 21/65* (2013.01); *G01J 3/28* (2013.01); *G01J 3/44* (2013.01); *G01J 3/10* (2013.01); *G01J 2003/2843* (2013.01)

(58) Field of Classification Search
CPC .... G01N 21/65; G01J 3/28; G01J 3/44; G01J 3/10; G01J 2003/2843
(Continued)

(56) References Cited

U.S. PATENT DOCUMENTS

| 8,873,041 B1* | 10/2014 | Chai | ...................... G01N 21/65 356/301 |
| 2010/0053606 A1* | 3/2010 | Matousek | ................. G01J 3/44 356/301 |

(Continued)

FOREIGN PATENT DOCUMENTS

| CN | 105699356 A | 6/2016 |
| WO | WO 2015/096788 A1 | 7/2015 |

OTHER PUBLICATIONS

Band-Target Entropy Minimization. A Robust Algorithm for Pure Component Spectral Recovery. Application to Complex Randomized Mixtures of Six Components, Widjaja et al,Anal. Chem., 2003, 75 (17), pp. 4499-4507 (Year: 2003).*

(Continued)

*Primary Examiner* — Kara E. Geisel
*Assistant Examiner* — Jonathon Cook
(74) *Attorney, Agent, or Firm* — Knobbe, Martens, Olson & Bear, LLP

(57) ABSTRACT

A Raman spectrum detecting method and electronic device are disclosed. In one aspect, an example method includes detecting and obtaining a first Raman spectrum signal of a package. A second Raman spectrum signal of the object is detected and obtained with the package. The first Raman spectrum signal is successively subtracting from the second Raman spectrum signal to obtain a series of third Raman spectrum signals with package interference eliminated. Information entropies of the third and first Raman spectrum signals are calculated and compared with information entropy of the first Raman spectrum signal. Information entropies of third Raman spectrum signals greater than the first Raman spectrum signal are set into an information entropy sequence to be selected, and a minimum information entropy from the sequence is selected. The third Raman spectrum signal corresponding to the minimum information (Continued)

entropy is used as an optimized Raman spectrum signal with package interference eliminated.

19 Claims, 5 Drawing Sheets

(51) Int. Cl.
*G01J 3/28* (2006.01)
*G01J 3/10* (2006.01)

(58) Field of Classification Search
USPC .......................................................... 356/301
See application file for complete search history.

(56) References Cited

U.S. PATENT DOCUMENTS

2015/0185154 A1* 7/2015 Chen ...................... G01N 21/65
356/301
2015/0339262 A1 11/2015 Wiegand et al.

OTHER PUBLICATIONS

Weighted two-band target entropy minimization for the reconstruction of pure component mass spectra: simulation studies and the application to real systems, Zhang et al, J Ann Soc Mass Spectrom 2003, 14, 1295-1305 (Year: 2003).*

Chew et al., "Band-target entropy minimization (BTEM): An advanced method for recovering unknown pure component spectra. Application to the FTIR spectra of unstable organometallic mixtures" Organometal, American Chemical Society dated Jan. 1, 2002.

Tan et al., "Wavelet analysis applied to removing non-constant, varying spectroscopic background in multivariate calibration", Journal of Chemometrics, dated Mar. 27, 2002.

Tan, et al., "Self-modeling curve resolution of multi-component vibrational spectroscopic data using automatic band-target entropy minimization (AutoBTEM)" Analytica Chimica ACTA dated Apr. 20, 2009.

Extended European Search Report issued for Application No. 17205839.8 dated May 17, 2018, which corresponds in priority to above-identified subject U.S. Application.

* cited by examiner

RAMAN SPECTRUM DETECTING METHOD FOR ELIMINATING PACKAGE INTERFERENCE AND ELECTRONIC DEVICE THEREOF

CROSS-REFERENCE TO RELATED APPLICATION

This application claims priority to Chinese Patent Application No. 201611127731.8 filed on Dec. 8, 2016, the disclosure of which is hereby incorporated by reference in its entirety for all purposes.

BACKGROUND OF THE DISCLOSED TECHNOLOGY

Field of the Technology

Embodiments of the disclosed technology generally relates to a field of Raman spectrum detection, and more particularly to a Raman spectrum detecting method for eliminating package interference and an electronic device therefor.

Description of the Related Technology

Raman spectrum is a molecular vibration spectrum, which may reflect molecular fingerprint characteristics and may be used for a detection of substances. A Raman spectrum detection method can detect and identify substances by detecting the Raman spectrum generated by the Raman scattering effect of an object upon being excited by excitation light. This Raman spectrum detecting method has been widely used in liquid security inspection, jewelry detection, explosives detection, drug detection, medicine detection, pesticide residue detection and other fields.

One of the problems encountered in detection of substances by the Raman spectrum detecting method is the detection of an object contained in a package. Since the object sometimes needs to be contained in a package or even packaged in the package, it is inevitable that the detection will be interfered by the package (such as bags, glass bottles, plastic bottles, etc.). In order to obtain the Raman spectrum of the object contained in a package, excitation light is required to firstly pass through the package. A package made of a material such as plastic, glass, or the like will generate some signals itself upon being excited by the excitation light, which may result in large difference between the obtained Raman spectrum and the Raman spectrum of the object itself leading to inaccurate identification for lots of substances. Currently there is no good solution for eliminating the interference of the package, and an object often has to be taken out of the package for detection, which is not convenient for operation.

Therefore, elimination of the interference of package in Raman spectrum detection to obtain the Raman spectrum of the object accurately and to realize accurate identification of the object is important for improving accuracy of Raman spectrum detection in various application fields.

SUMMARY

The disclosed technology has been made in order to overcome at least one of the above and other problems and deficiencies existing in the prior art.

At least one object of the disclosed technology is to provide a Raman spectrum detecting method for eliminating package interference and an electronic device therefor, which can effectively eliminate the interference of the Raman spectrum of the package to the Raman spectrum signal of the object so as to accurately detect and identify the Raman spectrum of the object.

According to one aspect of the disclosed technology, there is provided a Raman spectrum detecting method for eliminating package interference, comprising steps of:

detecting a Raman spectrum of a package to obtain a Raman spectrum signal representing the Raman spectrum of the package;

detecting a Raman spectrum of an object in the package passing through the package to obtain a Raman spectrum signal representing the Raman spectrum of the object together with the package;

successively subtracting the Raman spectrum signal of the package from the Raman spectrum signal of the object together with the package to obtain a series of package-interference-eliminated Raman spectrum signals;

calculating the information entropy of each of the series of package-interference-eliminated Raman spectrum signals and the information entropy of the Raman spectrum signal of the package;

comparing the information entropies of the series of package-interference-eliminated Raman spectrum signals with the information entropy of the Raman spectrum signal of the package, setting the information entropies of package-interference-eliminated Raman spectrum signals that are each greater than the information entropy of the Raman spectrum signal of the package into an information entropy sequence to be selected, and selecting a minimum information entropy from the information entropy sequence; and using the package-interference-eliminated Raman spectrum signal corresponding to the minimum information entropy as an optimized package-interference-eliminated Raman spectrum signal.

According to some embodiments, the step of successively subtracting the Raman spectrum signal of the package from the Raman spectrum signal of the object together with the package to obtain a series of package-interference-eliminated Raman spectrum signals comprises: subtracting a product of a proportionality coefficient and the Raman spectrum signal of the package from the Raman spectrum signal of the object together with the package, and successively changing the proportionality coefficient to successively subtract the Raman spectrum signal of the package from the Raman spectrum signal of the object together with the package.

According to some embodiments, the Raman spectrum signal of the package is a discrete data sequence A, and the Raman spectrum signal of the object together with the package is a discrete data sequence B, and subtracting a product of a proportionality coefficient and the Raman spectrum signal of the package from the Raman spectrum signal of the object together with the package is performed according to the following formula:

$$C = B - j*K*A,$$

where C is a discrete data sequence representing the package-interference-eliminated Raman spectrum signal, j successively takes values of 1, 2, 3, . . . N, j is a natural number, N is a preset number of calculations, K is a preset eliminating proportion, and J*K represents the proportionality coefficient.

According to some embodiments, the method further comprises steps of: determining a position of a characteristic peak of the Raman spectrum of the package, and setting an interval including the position of the characteristic peak of the Raman spectrum of the package as a calculation interval;

wherein the step of successively subtracting the Raman spectrum signal of the package from the Raman spectrum signal of the object together with the package to obtain a series of package-interference-eliminated Raman spectrum signals comprises: within the calculation interval, successively subtracting the Raman spectrum signal of the package from the Raman spectrum signal of the object together with the package to obtain a series of package-interference-eliminated Raman spectrum signals.

According to some embodiments, the step of calculating the information entropy comprises:

calculating the information entropy of the Raman spectrum signal according to the following information entropy calculation formula:

$$H = -\Sigma_{i=1}^{n} p(x_i) \log_2 p(x_i),$$

where i represents the $i^{th}$ wave number of the Raman spectrum signal, n represents the signal length of the Raman spectrum signal, $x_i$ represents the intensity corresponding to the $i^{th}$ wave number, and $p(x_i)$ represents the probability of taking the intensity $x_i$ in the Raman spectrum signal.

According to some embodiments, the method further comprises a step of: before subtracting the Raman spectrum signal of the package from the Raman spectrum signal of the object together with the package, normalizing the Raman spectrum signal of the package and the Raman spectrum signal of the object together with the package.

According to some embodiments, K ranges from 0.005 to 0.03, and N ranges from 200 to 600.

According to another aspect of the disclosed technology, there is provided a Raman spectrum detecting method for eliminating a package interference comprising steps of:

detecting a Raman spectrum of a package to obtain a Raman spectrum signal representing the Raman spectrum of the package;

detecting a Raman spectrum of an object in the package passing through the package to obtain a Raman spectrum signal representing the Raman spectrum of the object together with the package;

normalizing the Raman spectrum signal of the package and the Raman spectrum signal of the object together with the package;

determining a position of a characteristic peak of the Raman spectrum of the package, and setting an interval including the position of the characteristic peak of the Raman spectrum of the package as a calculation interval;

within the calculation interval, successively subtracting a product of the normalized Raman spectrum signal of the package and a proportionality coefficient from the normalized Raman spectrum signal of the object together with the package and successively changing the proportionality coefficient to obtain a series of package-interference-eliminated interval Raman spectrum signals, within the calculation interval, calculating the information entropy of each of the series of package-interference-eliminated interval Raman spectrum signals and the information entropy of the Raman spectrum signal of the package;

comparing the information entropies of the series of package-interference-eliminated interval Raman spectrum signals with the information entropy of the Raman spectrum signal of the package, setting information entropies of package-interference-eliminated interval Raman spectrum signals within the calculation that are each greater than the information entropy of the Raman spectrum signal of the package into an information entropy sequence to be selected; selecting a minimum information entropy from the information entropy sequence, and selecting the proportionality coefficient corresponding to the minimum information entropy as an optimized proportionality coefficient; and subtracting a product of the normalized Raman spectrum signal of the package and the optimized proportionality coefficient from the normalized Raman spectrum signal of the object together with the package to obtain an optimized package-interference-eliminated Raman spectrum signal.

According to a further aspect of the disclosed technology, there is provided an electronic device comprising a memory for storing executable instructions and a processor for executing the executable instructions stored in the memory to perform the methods of any of the aspects or embodiments of the disclosed technology.

DETAILED DESCRIPTION OF CERTAIN ILLUSTRATIVE EMBODIMENTS

Figure 1:
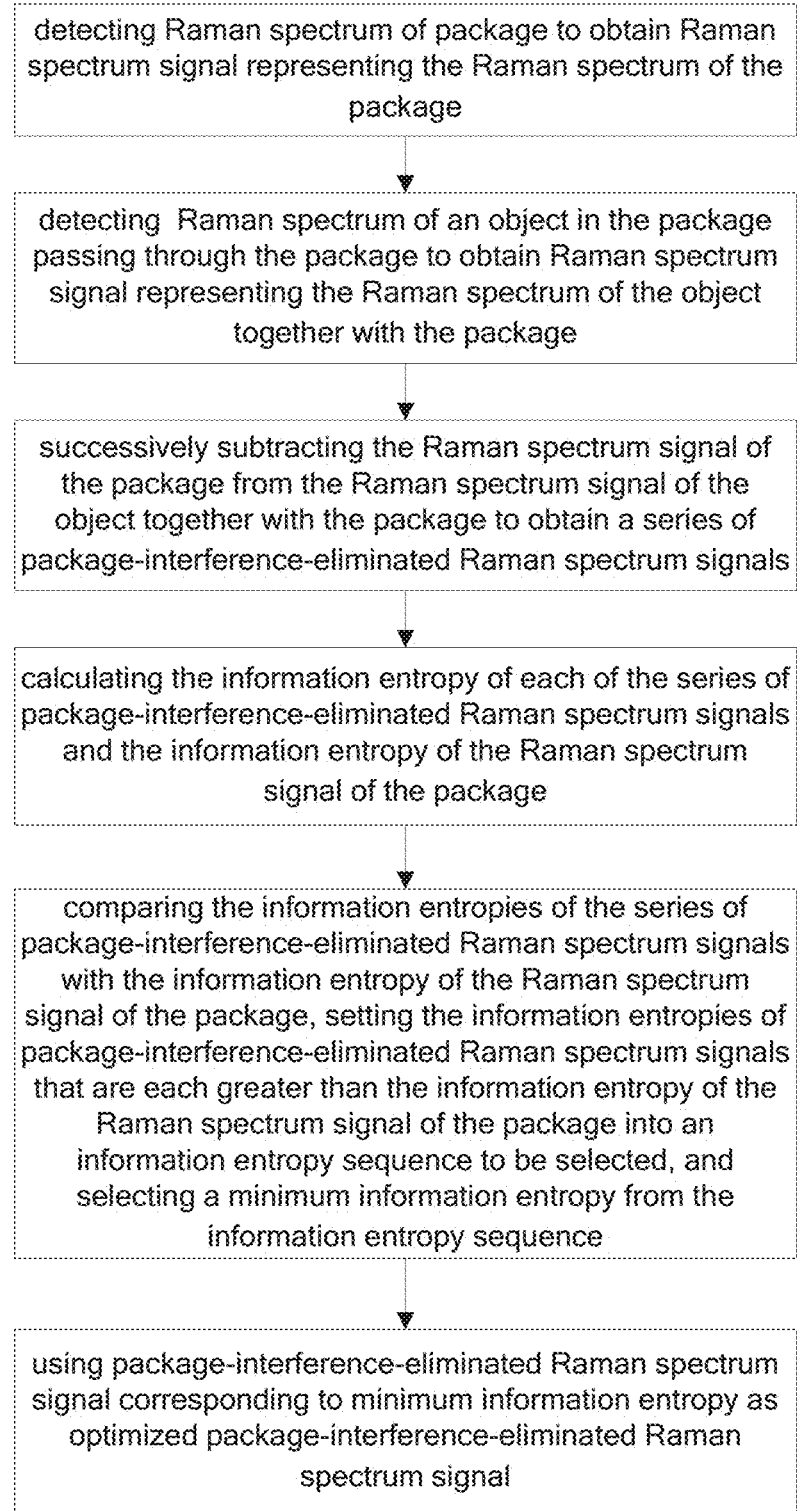
FIG. 1 schematically shows a flow chart of a Raman spectrum detecting method for eliminating package interference according to an embodiment of the disclosed technology.

The technical solutions of the disclosed technology will be further described below with reference to the embodiments and with reference to the accompanying drawings. In the description, the same or similar reference numerals represent the same or similar components. The following description of the embodiments of the disclosed technology with reference to the accompanying drawings is intended to explain the general concept of the disclosed technology, and should not be construed as a limitation to the disclosed technology.

Herein, the steps of the method are described by "first", "second", "A, B, C" and the like, for the convenience of description. However, unless expressly stated otherwise, such expression should not be construed as a limitation to the sequence for executing the steps.

When an object or sample is detected by the Raman spectrum, the object or sample sometimes needs to be contained in a package, such as bags, bottles, boxes, cans, and the like, especially when the object or sample is in a form of a liquid, gas or powdered solid. Thus, the detection of an object may require that the excitation light for detection is irradiated through the package onto the object, whereas the package may also generate Raman scattering effects upon being excited by the excitation light, in which case the package may generate interference to the Raman spectrum signal of the object or sample itself. Eliminating of such interference is important for accurate and effective detection and identification of the object or sample.

FIG. 1 schematically shows a flow chart of a Raman spectrum detecting method for eliminating package interference according to an embodiment of the disclosed technology. The method includes:

a step of obtaining a Raman spectrum signal of a package: detecting a Raman spectrum of the package to obtain a Raman spectrum signal A representing the Raman spectrum of the package;

a step of obtaining a Raman spectrum signal of an object together with the package: detecting a Raman spectrum of an object in the package passing through the package to obtain a Raman spectrum signal B representing the Raman spectrum of the object together with the package;

a step of obtaining a package-interference-eliminated Raman spectrum signal: subtracting the Raman spectrum signal A of the package from the Raman spectrum signal B of the object together with the package to obtain a series of Raman spectrum signals C with package interference eliminated;

a step of calculating information entropy: calculating an information entropy of each of the series of package-interference-eliminated Raman spectrum signals C and the information entropy of the Raman spectrum signal A of the package;

a step of selecting a minimum information entropy: comparing the information entropies of the series of package-interference-eliminated Raman spectrum signals C and the information entropy of the Raman spectrum signal A of the package, setting information entropies of package-interference-eliminated Raman spectrum signals C that are each greater than the information entropy of the Raman spectrum signal A of the package into an information entropy sequence to be selected; and selecting a minimum information entropy from the information entropy sequence; and a step of obtaining an optimized package-interference-eliminated Raman spectrum signal: using the package-interference-eliminated Raman spectrum signal C corresponding to the minimum information entropy as the optimized package-interference-eliminated Raman spectrum signal.

Specifically, in the step of obtaining the Raman spectrum signal of the package, the obtained Raman spectrum signal A of the package is a discrete data sequence denoted by $A_i$, where i successively takes values of 1, 2, 3, . . . n, and i is a natural number, and n represents the total number of data points in the data sequence. For example, the discrete data sequence $A_i$, may be a vector or matrix constituted by peak intensity data of a set of discrete Raman spectrum signals of the package. Similarly, in the step of obtaining the Raman spectrum signal of the object together with the package, the obtained Raman spectrum signal B of the object together with the package is also a discrete data sequence denoted by $B_i$, for example, a vector or matrix constituted by peak intensity data of a set of discrete Raman spectrum signals of the object together with the package.

In one example, the step of obtaining the package-interference-eliminated Raman spectrum signal specifically comprises: successively subtracting a product of "j*K" and the Raman spectrum signal A of the package from the Raman spectrum signal B of the object together with the package to obtain a series of Raman spectrum signals $C_j$ with package interference eliminated, where j successively takes values of 1, 2, 3, . . . N and j is a natural number, N is a preset number of calculations, K is a preset eliminating proportion, and J*K represents the proportionality coefficient. That is, $C_j$=B-j*K*A, wherein j successively takes values of 1, 2, 3, . . . N and j is a natural number. Accordingly, the series of package-interference-eliminated Raman spectral signals C include Raman spectral signals $C_1, C_2, C_3, \ldots, C_N$. It should be understood that each package-interference-eliminated Raman spectrum signal is also a discrete data sequence which also includes n data points.

According to an embodiment of the disclosed technology, the step of calculating information entropy includes: calculating the information entropy of the Raman spectrum signal according to the following information entropy calculation formula:

$$H=-\Sigma_{i=1}^{n}p(x_i)\log_2 p(x_i),$$

where i represents the $i^{th}$ wave number of the Raman spectrum signal, n represents a signal length of the Raman spectrum signal, $x_i$ represents the intensity corresponding to the $i^{th}$ wave number, and $p(x_i)$ represents the probability of taking the intensity $x_i$ in the Raman spectrum signal.

According to the theory of information entropy, information entropy evaluates the average amount of information of a random variable (for example, X) being equal to respective values, that is, the uncertainty of the random variable X. For a discrete data sequence, uniform distribution should be the most uncertain because there is no bias in the uniform distribution in discrete cases. For example, considering the binary case, that is, in the case for which the random variable X only has two cases X=a or X=b. If the probability of p (X=a) is large and close to 1 and the probability of p(X=b) is small, then in this case, it is obvious that the uncertainty of X is small due to the relative large certainty of X=a. Therefore, it should be understood that binary should be the most chaotic state at the same probability of occurrence. That is to say, the random variable X has the largest information entropy under uniform discrete distribution.

Specifically, when eliminating the package interference information, since the Raman spectrum signal of the package itself tends to distribute uniformly, the process of subtracting the Raman spectrum signal of the package from the Raman spectrum signal of the object together with the package is a process of eliminating uniformly distributed signals, that is, a process of changing the Raman spectrum signal from a relatively smooth signal into a non-smooth signal. Further, if the information is excessively eliminated, some characteristic peaks of the Raman spectrum signal of the object together with the package will be eliminated, which will in turn smooth the spectrum signal. According to the above theory, smoother Raman spectrum signal corresponds to larger information entropy. Therefore, in the process of successively eliminating the package interference, when the minimum information entropy is obtained, it means that the package interference information is completely eliminated at this point. Further, since the Raman spectrum signal of the package has fewer characteristic peaks, that is, it should have smaller information entropy, and the Raman spectrum signal of the object or sample generally has more characteristic peaks than the Raman spectrum signal of the package. Therefore, the information entropy of the Raman spectrum signal of the object or sample should be greater than the information entropy of the Raman spectrum signal of the package. Therefore, in an embodiment of the disclosed technology, when selecting the minimum information entropy, the information entropies of the series of package-interference-eliminated Raman spectrum signals are firstly compared with the information entropy of the Raman spectrum signal of the package, then information entropies of a package-interference-eliminated Raman spectrum signal that are each greater than the information entropy of the Raman spectrum signal of the package are set or grouped into an information entropy sequence to be selected, and a minimum information entropy is selected from the information entropy sequence. It can be seen from the above analysis that the minimum information entropy corresponds to optimized elimination of the Raman spectrum signal of the package from the Raman spectrum signal of the object together with the package.

In some embodiments, the Raman spectrum detecting method for eliminating package interference described above may further include the following steps: normalizing the Raman spectrum signal A of the package and the Raman spectrum signal B of the object together with the package. Normalization is to process data to be processed by certain normalization algorithm to a limited range, which enables the data in two different reference systems to be compared, calculated, and the like, for facilitating subsequent data processing and speeding up the convergence of subsequent calculations. Specifically, for example, the Raman spectrum signal A of the package may be normalized into a form consistent with the Raman spectrum signal B of the object together with the package so as to facilitate subsequent calculation of successively subtracting the Raman spectrum signal A of the package from the Raman spectrum signal B of the object together with the package.

Figure 2:
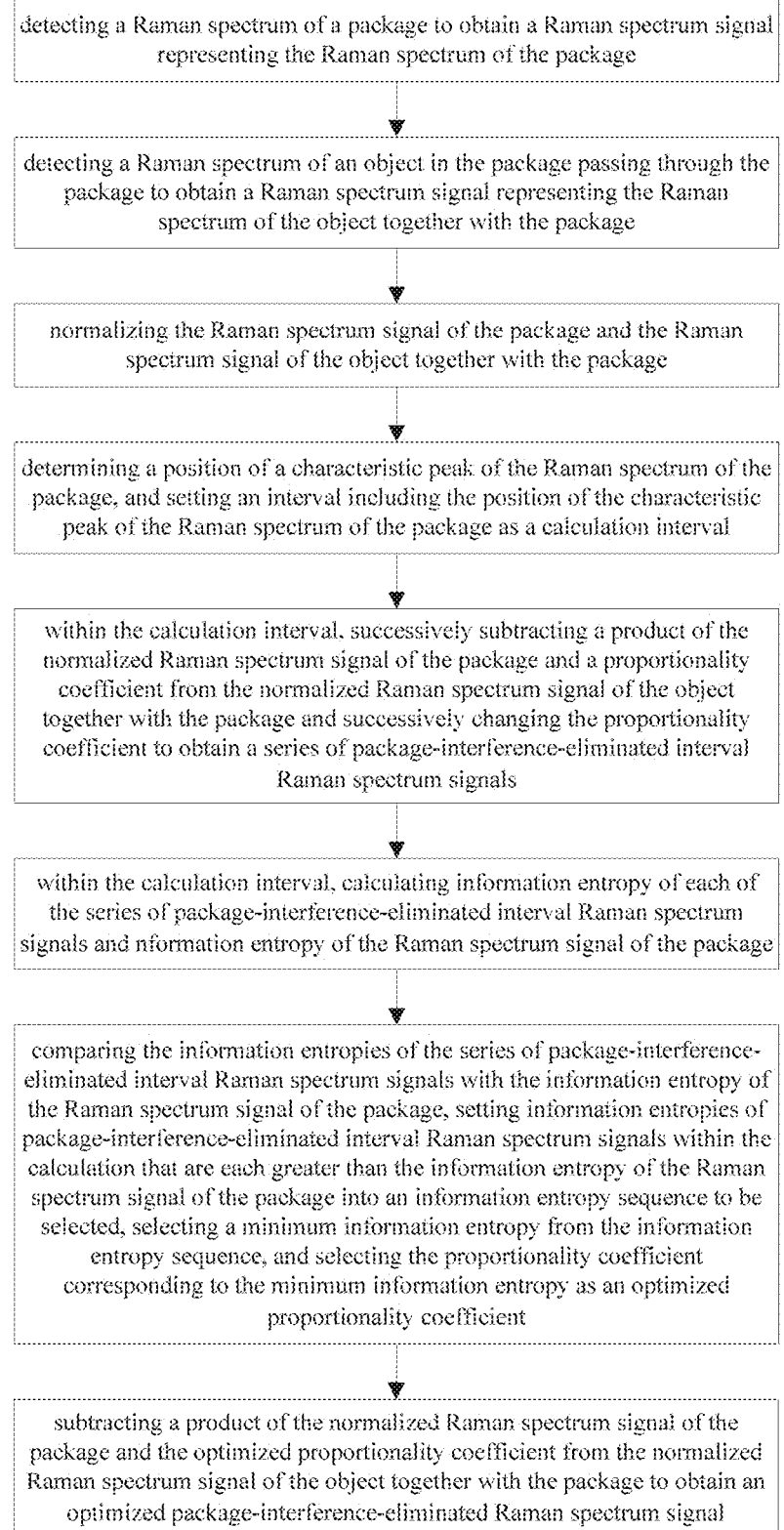
FIG. 2 schematically shows a flow chart of the Raman spectrum detecting method for eliminating package interference according to another embodiment of the disclosed technology.

According to some embodiments of the disclosed technology, the calculation of the information entropy may be performed just within an interval where the characteristic peaks of the Raman spectrum signal of the package are located, so as to reduce the amount of calculation and speed up the detection. FIG. 2 schematically shows a flow chart of a Raman spectrum detecting method for eliminating package interference according to another embodiment of the disclosed technology. In this embodiment, the Raman spectrum detecting method for eliminating package interference comprising:

a step of obtaining a Raman spectrum signal of the package: detecting a Raman spectrum of the package to obtain a Raman spectrum signal A representing the Raman spectrum of the package;

a step of obtaining a Raman spectrum signal of the object together with the package: detecting a Raman spectrum of an object or in the package passing through the package to obtain a Raman spectrum signal B representing the Raman spectrum of the object together with the package;

a step of normalizing: normalizing the Raman spectrum signal A of the package and the Raman spectrum signal B of the object together with the package;

a step of determining calculation interval: determining a position of a characteristic peak of the Raman spectrum of the package, and setting an interval including the position of the characteristic peak of the Raman spectrum of the package as the calculation interval;

a step of obtaining a package-interference-eliminated interval Raman spectrum signal within the calculation interval: successively subtracting a product of the normalized Raman spectrum signal A of the package and a preset proportionality coefficient from the normalized Raman spectrum signal B of the object together with the package within the calculation interval and changing the proportionality coefficient successively to obtain a series of interval Raman spectrum signals C' with package interference eliminated within the calculation interval;

a step of calculating information entropy: within the calculation interval, calculating the information entropy of each of the series of package-interference-eliminated interval Raman spectrum signals C' and the information entropy of the Raman spectrum signal A of the package;

a step of determining an optimized proportionality coefficient: comparing the information entropies of the series of package-interference-eliminated interval Raman spectrum signals with the information entropy of the Raman spectrum signal of the package, setting or grouping information entropies of package-interference-eliminated interval Raman spectrum signals C' that are each greater than the information entropy of the Raman spectrum signal A of the package into an information entropy sequence to be selected; selecting a minimum information entropy from the information entropy sequence, and selecting the proportionality coefficient corresponding to the minimum information entropy as the optimized proportionality coefficient; and a step of obtaining an optimized package-interference-eliminated Raman spectrum signal: subtracting a product of the normalized Raman spectrum signal A of the package and the optimized proportionality coefficient from the normalized Raman spectrum signal B of the object together with the package to obtain an optimized Raman spectrum signal with package interference eliminated.

Figure 3:
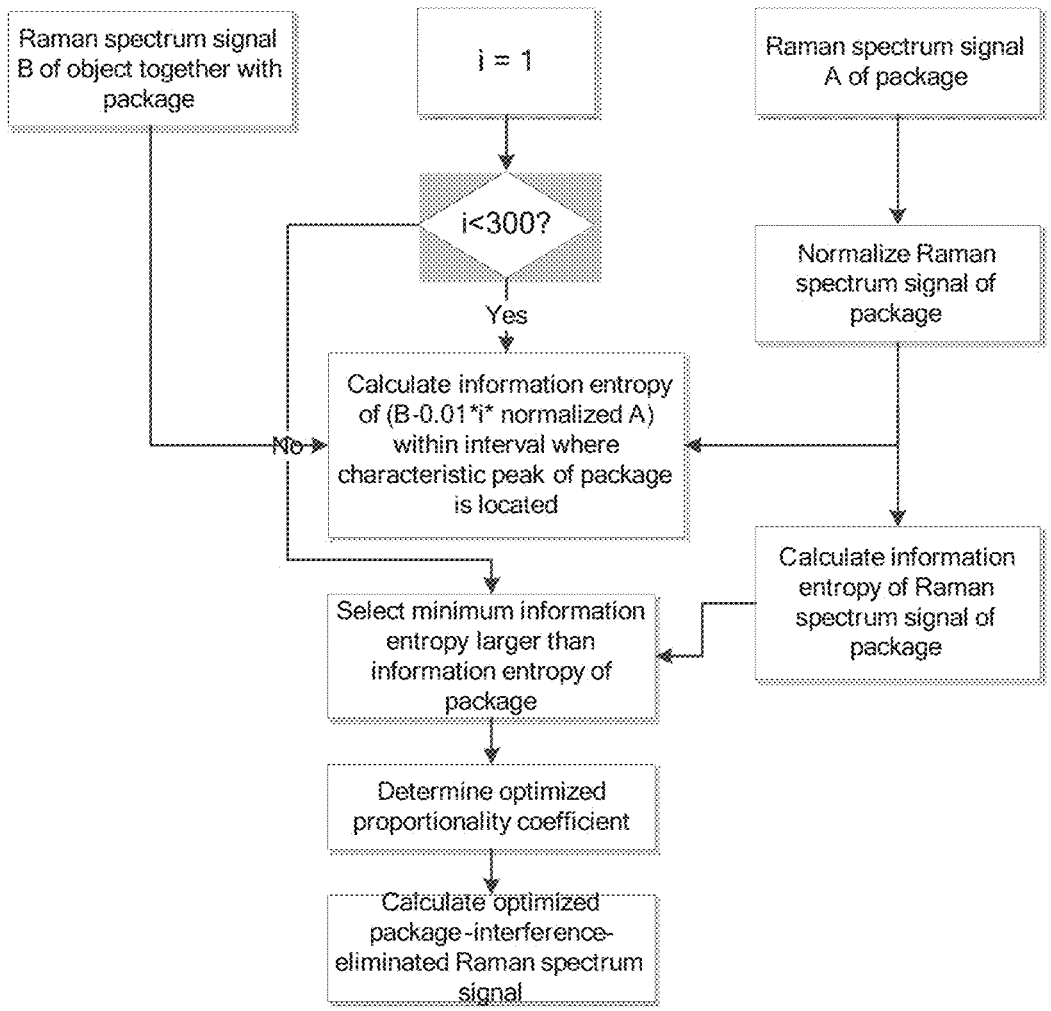
FIG. 3 schematically shows a flow chart of applying the Raman spectrum detecting method for eliminating package interference according to an embodiment of the disclosed technology.
Figure 4:
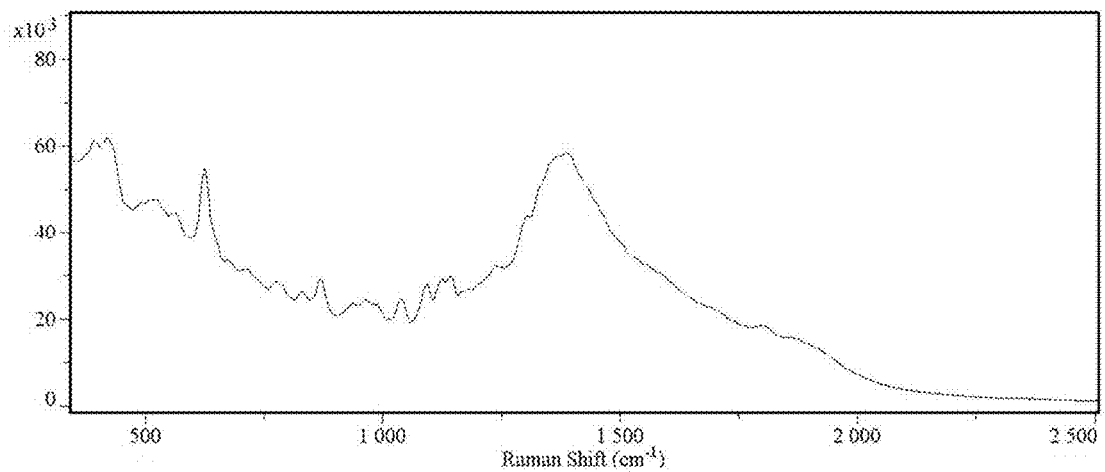
FIG. 4 schematically shows the Raman spectrum of an object together with a package.

In the following, as an example, the package is a glass bottle, a Raman spectrum detecting method for eliminating package interference according to an embodiment of the disclosed technology will be described in detail with reference to FIGS. 3-6. As shown in FIG. 3, the method may include the following steps:

A step of obtaining a Raman spectrum signal of the package includes: detecting a Raman spectrum of the package itself to obtain the Raman spectrum signal A representing the Raman spectrum of the package, as shown in FIG. 4, in which the horizontal coordinate value indicates the Raman shift or wave number (in $cm^{-1}$) and the vertical coordinate value indicates the intensity (dimensionless), so that the Raman spectrum signal A may be a vector including several discrete intensity values indicated by the vertical coordinate values shown in FIG. 4, or a matrix including several discrete Raman shifts indicated by the horizontal coordinate values shown in FIG. 4 and intensity values indicated by the corresponding vertical coordinate values.

Figure 5:
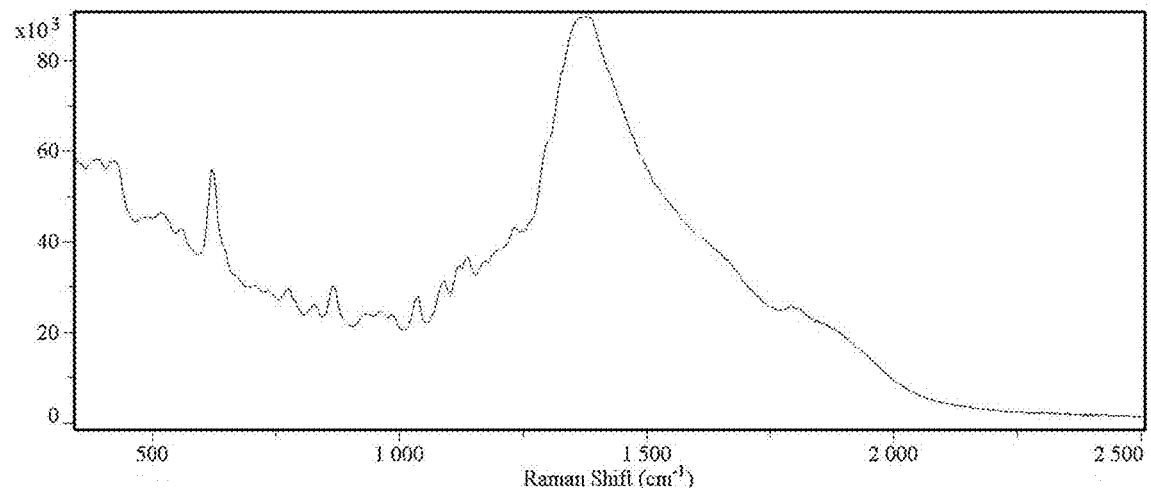
FIG. 5 schematically shows the Raman spectrum of the package.

A step of obtaining a Raman spectrum signal of an object together with the package includes: detecting a Raman spectrum of an object in the package passing through the package to obtain a Raman spectrum signal B representing the Raman spectrum of the object together with the package, as shown in FIG. 5, the horizontal and vertical axes have the same meanings as those of FIG. 4. Similarly, the Raman spectrum signal B may be a vector including several discrete intensity values indicated by the vertical coordinate values shown in FIG. 5, or a matrix including several discrete Raman shifts indicated by the horizontal coordinate values shown in FIG. 5 and intensity values indicated by the corresponding vertical coordinate values.

A step of normalizing includes: normalizing the Raman spectrum signal A of the package and the Raman spectrum signal B of the object together with the package. Specifically, if the horizontal coordinate value of the Raman spectrum signal A is not corresponding to the horizontal coordinate value of the Raman spectrum signal B, that is, the Raman spectrum signal A and the Raman spectrum signal B include intensity data that are not at the same Raman shift position, then intensity data of other Raman shift positions may be calculated based on the original data of Raman spectrum signals A and B through interpolation calculation, to convert the Raman spectrum signals A and B to the same Raman shift position. For example, in an embodiment, a Raman shift position may be set to be [350: 2: 2800] $cm^{-1}$, where 350 $cm^{-1}$ and 2800 $cm^{-1}$ represent the minimum and maximum Raman shift positions, respectively, "2" Represents an interval step, that is, the Raman shift positions are 350, 352, 354, 356 $cm^{-1}$, and so on, up to 2800 $cm^{-1}$. Then, if intensity data at these Raman shift positions are not included in the original data of the Raman spectrum signals A, B, then intensity data at these Raman shift positions may be calculated based on the original data of Raman spectrum signals A and B through interpolation calculation, so that the Raman spectrum signals A, B are converted to the same Raman shift position [350: 2: 2800] $cm^{-1}$, and the converted Raman spectrum signals A and B are respectively indicated as Raman spectrum signals A' and B'. And, if the vertical coordinate value of the Raman spectrum signal A is not corresponding to the vertical coordinate value of the Raman spectrum signal B, that is, the intensity data of the Raman spectrum signal A and the Raman spectrum signal B are not located in a same reference system or are measured in different intervals or ranges, the Raman spectrum signal A' may be converted into a form consistent with the Raman spectrum signal B'. For example, in one embodiment, the maximum values max (A'), max (B') of vertical coordinate values of the Raman spectrum signals A', B' may be selected respectively, and a ratio of max (A') and max (B') is used as a normalizing coefficient of the vertical coordinate, the discrete data of the Raman spectrum signal A' are respectively multiplied by the normalizing coefficient to convert the Raman spectrum signal A' into the form consistent with the Raman spectrum signal B', and the converted Raman spectrum signal A' is indicated as a Raman spectrum signal A''. In other embodiments, the Raman spectrum signal B may also be kept unchanged, and the Raman spectrum signal A is directly normalized into a form consistent with the Raman spectrum signal B.

A step of determining calculation interval includes: determining a position of a characteristic peak of the Raman spectrum of the package, and setting an interval or range including the position of the characteristic peak of the Raman spectrum of the package as a calculation interval. In the embodiment shown in FIG. 4, for example, it can be determined that the position of the characteristic peak of the package is mainly in the interval of 1000 $cm^{-1}$ to 1700 $cm^{-1}$, so the interval of 1000 $cm^{-1}$ to 1700 $cm^{-1}$ may be determined or set as the calculation interval.

A step of obtaining a package-interference-eliminated Raman spectrum signal includes: successively subtracting a product of the normalized Raman spectrum signal A'' of the package and a preset proportionality coefficient from the normalized Raman spectrum signal B' of the object together with the package within the calculation interval of 1000 $cm^{-1}$ to 1700 $cm^{-1}$ and changing the proportionality coefficient successively to obtain a series of package-interference-eliminated interval Raman spectrum signals C within the calculation interval.

A step of calculating information entropy includes: within the calculation interval, calculating the information entropy of each of the series of package-interference-eliminated interval Raman spectrum signals C and the information entropy of the Raman spectrum signal A'' of the package. Specifically, the calculating process of the above two steps can be expressed by the following formula:

$$C_j = B' - j*K*A''$$

where j successively takes values of 1, 2, 3, ... N and j is a natural number, N is a preset number of calculations, and K is a preset eliminating proportion, and J*K is successively changed through successively changing j, that is, J*K represents the proportionality coefficient KK which is successively changed. In some embodiments, K is in the range of 0.005 to 0.03, and N is in the range of 200 to 600. Preferably, in one example, N is set to be 300 and K is set to be 0.01. When N and K take such values, the minimum information entropy may be calculated faster without excessively increasing the calculation time. In this way, by successively changing the value of j, the Raman spectrum signal A'' of the package may be successively subtracted from the Raman spectrum signal B' of the object together with the package at a step of 0.01 to obtain 300 package-interference-eliminated interval Raman spectrum signals C within the calculation interval.

Then, the information entropy of each of the series of package-interference-eliminated interval Raman spectrum signals $C_j$ and the information entropy of the Raman spectrum signal A'' of the package are calculated according to the following information entropy calculation formula. Since there are 300 package-interference-eliminated interval Raman spectrum signals C, the information entropies of the 300 interval Raman spectral signals C may be calculated correspondingly.

$$H = -\Sigma_{i=1}^{n} p(x_i) \log_2 p(x_i),$$

where i represents the $i^{th}$ wave number of the Raman spectrum signal, n represents the signal length of the Raman spectrum signal, $x_i$ represents the intensity corresponding to the $i^{th}$ wave number, and $p(x_i)$ represents the probability of taking the intensity $x_i$ in the Raman spectrum signal.

A step of determining an optimized proportionality coefficient includes: comparing the information entropies of the series of package-interference-eliminated interval Raman spectrum signals with the information entropy of the Raman spectrum signal of the package, setting or grouping information entropies of package-interference-eliminated interval Raman spectrum signal that are each greater than the information entropy of the Raman spectrum signal of the package into an information entropy sequence to be selected; selecting a minimum information entropy from the information entropy sequence, and selecting the proportionality coefficient corresponding to the minimum information entropy as the optimized proportionality coefficient, which is indicated as $KK_{optimized}$.

In the above calculating process, by setting the calculation interval to be an interval including the position of the characteristic peak of the package, the amount of calculation can be greatly reduced, so as to speed up the detection.

Figure 6:
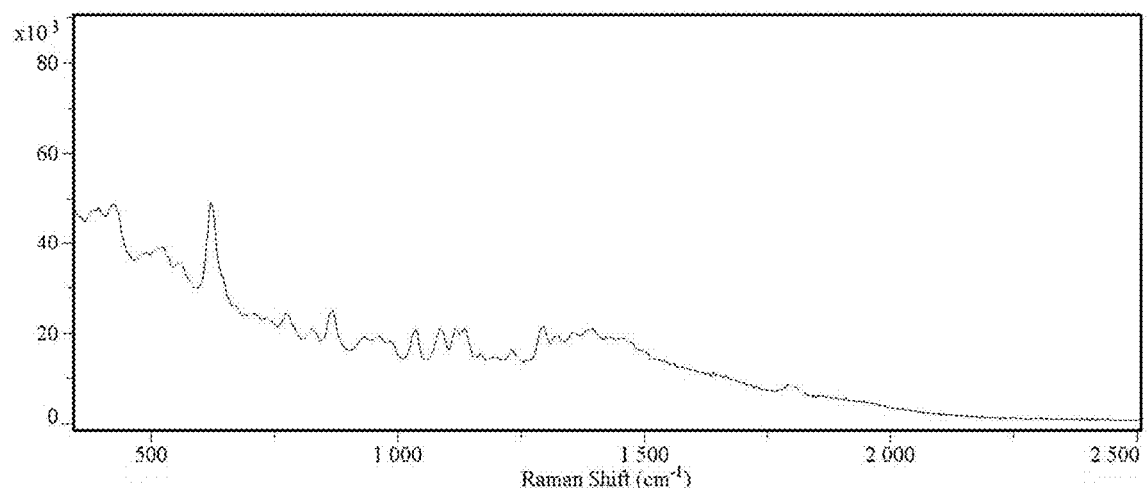
FIG. 6 schematically shows the Raman spectrum of the object with the package interference eliminated from the Raman spectrum of the object together with the package by using the Raman spectrum detecting method of the embodiment of the disclosed technology.

A step of obtaining an optimized package-interference-eliminated Raman spectrum signal includes: subtracting a product of the Raman spectrum signal A'' of the package and the optimized proportionality coefficient from the Raman spectrum signal B' of the object together with the package to obtain an optimized Raman spectrum signal $C_{optimized}$ with package interference eliminated, that is, $C_{optimized} = B' - KK_{optimized}*A''$. By putting the corresponding data in FIGS. 4-5 into such formula, data of optimized Raman spectrum signal $C_{optimized}$ with package interference eliminated may be obtained. An optimized package-interference-eliminated Raman spectra graph graphed according to these data is shown in FIG. 6. Comparing FIG. 4 and FIG. 6, it can be seen that the Raman spectrum $C_{optimized}$ has a relatively well elimination of the package interference signal.

Figure 7:
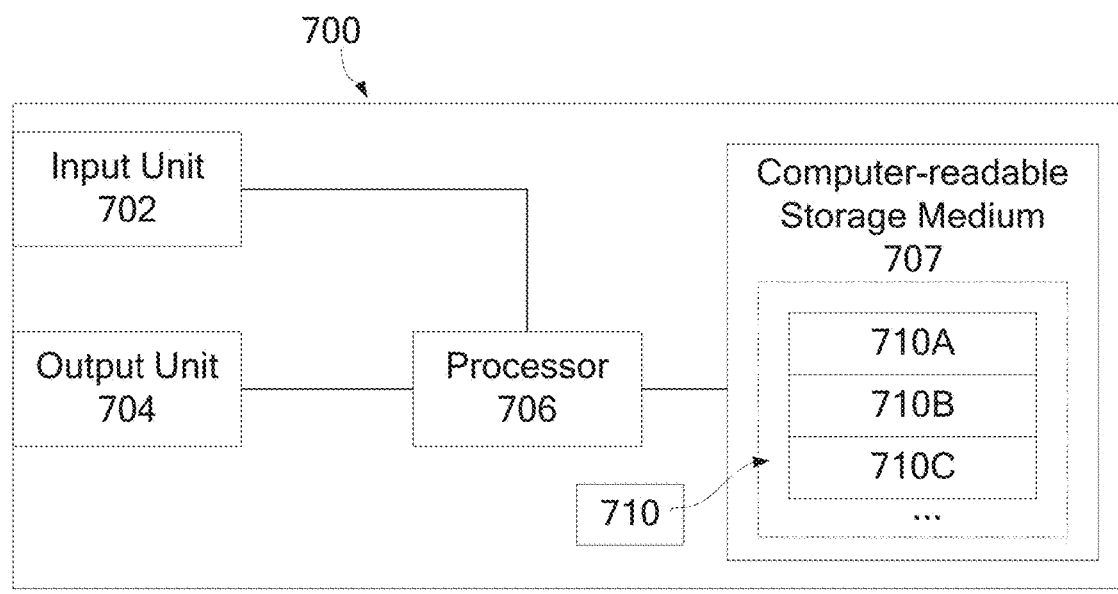
FIG. 7 shows a block diagram illustrating an exemplary hardware arrangement of an electronic device for performing the method according to the embodiments of the disclosed technology.

According to yet another embodiment of the disclosed technology, there is also provided an electronic device. FIG. 7 shows a block diagram illustrating an exemplary hardware arrangement of an electronic device 700. The electronic device 700 includes a processor 706 (e.g., a microprocessor (μP), a digital signal processor (DSP), or the like). The processor 706 may be or include a single processing unit or a plurality of processing units for performing different actions of the steps described herein. The electronic device 700 may also include an input unit 702 for receiving signals from other devices, and an output unit 704 for providing signals to other devices. The input unit 702 and the output unit 704 may be arranged as a single device or as separate devices.

In addition, the electronic device 700 may include at least one computer-readable storage medium 707 in the form of non-volatile memory or volatile memory, such as electrically erasable programmable read only memory (EEPROM), flash memory, and/or hard disk drive. The computer-readable storage medium 707 includes or stores a computer program 710 that includes codes or computer-readable instructions that, when executed by the processor 706 in the electronic device 700, enable the electronic device 700 and/or an apparatus including the electronic device 700 to perform processes such as those described above in connection with FIGS. 1-3 and any variations thereof.

The computer program 710 may be configured as computer program codes having architectures such as computer program modules 710A-710C, and the like. The computer program modules may essentially perform various actions or steps in the flowchart illustrated in FIGS. 1-3 to simulate a device. In other words, when different computer program modules are executed in the processor 706, they may correspond to the above different units in the device.

Although the code means in the embodiments disclosed above in connection with FIG. 7 are implemented as computer program modules that, when executed in the processor 706, enable the electronic device 700 to perform the actions described above in connection with FIGS. 1-3, however, in other optional embodiments, at least one of the code means may be at least partially implemented as a hardware circuit.

The processor may be a single CPU (Central Processing Unit), but may also include two or more processing units. For example, the processor may include a general microprocessor, an instruction set processor and/or related chipsets and/or a specialized microprocessor (e.g., an application specific integrated circuit (ASIC)). The processor may also include an on-board memory for caching purposes. The computer program may be carried by a computer program product connected to the processor. The computer program product may include a computer readable medium having a computer program stored thereon. For example, the computer program product may be a flash memory, a random access memory (RAM), a read only memory (ROM), an EEPROM, and the above computer program modules, and in alternative embodiments, may be distributed in the form of memory in different computer program products.

In embodiments of the disclosed technology, the interference information caused by the package is eliminated from the Raman spectrum signal including spectrum signal of the package by calculating the minimum information entropy so that the Raman spectrum signal reflecting the property of the object itself may be obtained accurately. This allows accurate detection of the Raman spectrum of the packaged object and thus effective identification of the object.

It should be understood by those skilled in the art that in the embodiments of the disclosed technology, although the technical concept of the disclosed technology is described in detail by taking the glass bottle package as an example, the disclosed technology is not limited to eliminating the interference of the package of a glass bottle.

Although the disclosed technology has been described with reference to the accompanying drawings, the embodiments disclosed in the drawings are intended to illustrate the preferred embodiments of the disclosed technology, and should not be construed as limiting the disclosed technology.

Although some embodiments of the general concept of the disclosed technology have been shown and described, it will be understood by those of ordinary skill in the art that various changes may be made in these embodiments without departing from the spirit and scope of the general concept. Accordingly, the scope the disclosed technology is defined by the claims and their equivalents. The various features and processes described herein may be implemented independently of one another, or may be combined in various ways. All possible combinations and sub combinations are intended to fall within the scope of this disclosure. In addition, certain methods or process blocks may be omitted in some implementations. The methods and processes disclosed herein are also not limited to any particular sequence, and the blocks or states relating thereto can be performed in any other sequences that are appropriate. For example, described blocks or states may be performed in an order other than that specifically disclosed, or multiple blocks or states may be combined in a single block or state. The example blocks or states may be performed in serial, in parallel, or in some other manner as appropriate. Blocks or states may be added to or removed from the disclosed example embodiments as suitable. The example systems and components described herein may be configured differently than described. For example, elements may be added to, removed from, or rearranged compared to the disclosed example embodiments.

While certain embodiments have been described, these embodiments have been presented by way of example only, and are not intended to limit the scope of the disclosure. Indeed, the novel devices, systems, apparatus, methods, and systems described herein may be embodied in a variety of other forms; furthermore, various omissions, substitutions and changes in the form of the methods and systems described herein may be made without departing from the spirit of the disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. Any suitable combination of the elements and acts of the various embodiments described above can be combined to provide further embodiments.

What is claimed is:

1. A Raman spectrum detecting method for eliminating package interference, the method comprising:
 detecting a Raman spectrum of a package to obtain a Raman spectrum signal representing the Raman spectrum of the package;
 detecting a Raman spectrum of an object in the package passing through the package to obtain a Raman spectrum signal representing the Raman spectrum of the object together with the package;
 eliminating, based on the Raman spectrum signal representing the Raman spectrum of the package, uniformly distributed signals from the Raman spectrum signal representing the Raman spectrum of the object together with the package, such that the Raman spectrum signal is changed from a relatively smooth signal into a non-smooth signal;

successively subtracting the Raman spectrum signal of the package from the Raman spectrum signal of the object together with the package so as to obtain a series of package-interference-eliminated Raman spectrum signals;

calculating an information entropy of each of the series of package-interference-eliminated Raman spectrum signals and an information entropy of the Raman spectrum signal of the package;

comparing the information entropies of the series of package-interference-eliminated Raman spectrum signals with the information entropy of the Raman spectrum signal of the package, setting the information entropies of package-interference-eliminated Raman spectrum signals that are each greater than the information entropy of the Raman spectrum signal of the package into an information entropy sequence to be selected, and selecting a minimum information entropy from the information entropy sequence; and using the package-interference-eliminated Raman spectrum signal corresponding to the minimum information entropy as an optimized package-interference-eliminated Raman spectrum signal.

2. The Raman spectrum detecting method according to claim 1, wherein successively subtracting the Raman spectrum signal of the package from the Raman spectrum signal of the object together with the package to obtain a series of package-interference-eliminated Raman spectrum signals comprises:

subtracting a product of a proportionality coefficient and the Raman spectrum signal of the package from the Raman spectrum signal of the object together with the package, and successively changing the proportionality coefficient to successively subtract the Raman spectrum signal of the package from the Raman spectrum signal of the object together with the package.

3. The Raman spectrum detecting method according to claim 2, wherein calculating the information entropy comprises:

calculating the information entropy of the Raman spectrum signal according to the following information entropy calculation formula:

$$H = -\Sigma_{i=1}^{n} p(x_i) \log_2 p(x_i),$$

where i represents the $i^{th}$ wave number of the Raman spectrum signal, n represents the signal length of the Raman spectrum signal, $x_i$ represents the intensity corresponding to the $i^{th}$ wave number, and $p(x_i)$ represents the probability of taking the intensity $x_i$ in the Raman spectrum signal.

4. The Raman spectrum detecting method according to claim 2, further comprising:

before subtracting the Raman spectrum signal of the package from the Raman spectrum signal of the object together with the package, normalizing the Raman spectrum signal of the package and the Raman spectrum signal of the object together with the package.

5. The Raman spectrum detecting method according to claim 2, wherein the Raman spectrum signal of the package is a discrete data sequence A, and the Raman spectrum signal of the object together with the package is a discrete data sequence B, and subtracting a product of a proportionality coefficient and the Raman spectrum signal of the package from the Raman spectrum signal of the object together with the package is performed according to the following formula:

$$C = B - j*K*A,$$

where C is a discrete data sequence representing the package-interference-eliminated Raman spectrum signal, j successively takes values of 1, 2, 3, . . . N and j is a natural number, N is a preset number of calculations, K is a preset eliminating proportion, and J*K represents the proportionality coefficient.

6. The Raman spectrum detecting method according to claim 5, further comprising:

determining a position of a characteristic peak of the Raman spectrum of the package, and setting an interval including the position of the characteristic peak of the Raman spectrum of the package as a calculation interval;

wherein successively subtracting the Raman spectrum signal of the package from the Raman spectrum signal of the object together with the package to obtain a series of package-interference-eliminated Raman spectrum signals comprises:

within the calculation interval, successively subtracting the Raman spectrum signal of the package from the Raman spectrum signal of the object together with the package to obtain a series of package-interference-eliminated Raman spectrum signals.

7. The Raman spectrum detecting method according to claim 5, wherein calculating the information entropy comprises:

calculating the information entropy of the Raman spectrum signal according to the following information entropy calculation formula:

$$H = -\Sigma_{i=1}^{n} p(x_i) \log_2 p(x_i),$$

where i represents the $i^{th}$ wave number of the Raman spectrum signal, n represents the signal length of the Raman spectrum signal, $x_i$ represents the intensity corresponding to the $i^{th}$ wave number, and $p(x_i)$ represents the probability of taking the intensity $x_i$ in the Raman spectrum signal.

8. The Raman spectrum detecting method according to claim 5, further comprising:

before subtracting the Raman spectrum signal of the package from the Raman spectrum signal of the object together with the package, normalizing the Raman spectrum signal of the package and the Raman spectrum signal of the object together with the package.

9. The Raman spectrum detecting method according to claim 5, wherein K ranges from 0.005 to 0.03, and N ranges from 200 to 600.

10. The Raman spectrum detecting method according to claim 2, further comprising:

determining a position of a characteristic peak of the Raman spectrum of the package, and setting an interval including the position of the characteristic peak of the Raman spectrum of the package as a calculation interval;

wherein successively subtracting the Raman spectrum signal of the package from the Raman spectrum signal of the object together with the package to obtain a series of package-interference-eliminated Raman spectrum signals comprises:

within the calculation interval, successively subtracting the Raman spectrum signal of the package from the Raman spectrum signal of the object together with the package to obtain a series of package-interference-eliminated Raman spectrum signals.

11. The Raman spectrum detecting method according to claim 10, further comprising:
before subtracting the Raman spectrum signal of the package from the Raman spectrum signal of the object together with the package, normalizing the Raman spectrum signal of the package and the Raman spectrum signal of the object together with the package.

12. The Raman spectrum detecting method according to claim 1, further comprising:
determining a position of a characteristic peak of the Raman spectrum of the package, and setting an interval including the position of the characteristic peak of the Raman spectrum of the package as a calculation interval;
wherein successively subtracting the Raman spectrum signal of the package from the Raman spectrum signal of the object together with the package to obtain a series of package-interference-eliminated Raman spectrum signals comprises:
within the calculation interval, successively subtracting the Raman spectrum signal of the package from the Raman spectrum signal of the object together with the package to obtain a series of package-interference-eliminated Raman spectrum signals.

13. The Raman spectrum detecting method according to claim 12, wherein calculating the information entropy comprises:
calculating the information entropy of the Raman spectrum signal according to the following information entropy calculation formula:

$$H = -\Sigma_{i=1}^{n} p(x_i) \log_2 p(x_i),$$

where i represents the $i^{th}$ wave number of the Raman spectrum signal, n represents the signal length of the Raman spectrum signal, $x_i$ represents the intensity corresponding to the $i^{th}$ wave number, and $p(x_i)$ represents the probability of taking the intensity $x_i$ in the Raman spectrum signal.

14. The Raman spectrum detecting method according to claim 12, further comprising:
before subtracting the Raman spectrum signal of the package from the Raman spectrum signal of the object together with the package, normalizing the Raman spectrum signal of the package and the Raman spectrum signal of the object together with the package.

15. The Raman spectrum detecting method according to claim 1, wherein calculating the information entropy comprises:
calculating the information entropy of the Raman spectrum signal according to the following information entropy calculation formula:

$$H = -\Sigma_{i=1}^{n} p(x_i) \log_2 p(x_i),$$

where i represents the $i^{th}$ wave number of the Raman spectrum signal, n represents the signal length of the Raman spectrum signal, $x_i$ represents the intensity corresponding to the $i^{th}$ wave number, and $p(x_i)$ represents the probability of taking the intensity $x_i$ in the Raman spectrum signal.

16. The Raman spectrum detecting method according to claim 1, further comprising:
before subtracting the Raman spectrum signal of the package from the Raman spectrum signal of the object together with the package, normalizing the Raman spectrum signal of the package and the Raman spectrum signal of the object together with the package.

17. A Raman spectrum detecting method for eliminating package interference, the method comprising:
detecting a Raman spectrum of a package to obtain a Raman spectrum signal representing the Raman spectrum of the package;
detecting a Raman spectrum of an object in the package passing through the package to obtain a Raman spectrum signal representing the Raman spectrum of the object together with the package;
normalizing the Raman spectrum signal of the package and the Raman spectrum signal of the object together with the package;
determining a position of a characteristic peak of the Raman spectrum of the package, and setting an interval including the position of the characteristic peak of the Raman spectrum of the package as a calculation interval;
within the calculation interval, successively subtracting a product of the normalized Raman spectrum signal of the package and a proportionality coefficient from the normalized Raman spectrum signal of the object together with the package and successively changing the proportionality coefficient to obtain a series of package-interference-eliminated interval Raman spectrum signals;
within the calculation interval, calculating the information entropy of each of the series of package-interference-eliminated interval Raman spectrum signals and the information entropy of the Raman spectrum signal of the package;
comparing the information entropies of the series of package-interference-eliminated interval Raman spectrum signals with the information entropy of the Raman spectrum signal of the package, setting information entropies of package-interference-eliminated interval Raman spectrum signals within the calculation that are each greater than the information entropy of the Raman spectrum signal of the package into an information entropy sequence to be selected, selecting a minimum information entropy from the information entropy sequence, and selecting the proportionality coefficient corresponding to the minimum information entropy as an optimized proportionality coefficient; and
subtracting a product of the normalized Raman spectrum signal of the package and the optimized proportionality coefficient from the normalized Raman spectrum signal of the object together with the package to obtain an optimized package-interference-eliminated Raman spectrum signal.

18. An electronic device comprising:
a memory for storing executable instructions; and
a processor for executing the executable instructions stored in the memory to perform operations comprising:
detecting a Raman spectrum of a package to obtain a Raman spectrum signal representing the Raman spectrum of the package;
detecting a Raman spectrum of an object in the package passing through the package to obtain a Raman spectrum signal representing the Raman spectrum of the object together with the package;
eliminating, based on the Raman spectrum signal representing the Raman spectrum of the package, uniformly distributed signals from the Raman spectrum signal representing the Raman spectrum of the object together with the package, such that the Raman spectrum signal is changed from a relatively smooth signal into a non-smooth signal;

successively subtracting the Raman spectrum signal of the package from the Raman spectrum signal of the object together with the package so as to obtain a series of package-interference-eliminated Raman spectrum signals;

calculating an information entropy of each of the series of package-interference-eliminated Raman spectrum signals and an information entropy of the Raman spectrum signal of the package;

comparing the information entropies of the series of package-interference-eliminated Raman spectrum signals with the information entropy of the Raman spectrum signal of the package, setting the information entropies of package-interference-eliminated Raman spectrum signals that are each greater than the information entropy of the Raman spectrum signal of the package into an information entropy sequence to be selected, and selecting a minimum information entropy from the information entropy sequence; and using the package-interference-eliminated Raman spectrum signal corresponding to the minimum information entropy as an optimized package-interference-eliminated Raman spectrum signal.

19. An electronic device comprising:

a memory for storing executable instructions; and a processor for executing the executable instructions stored in the memory to perform operations comprising:

detecting a Raman spectrum of a package to obtain a Raman spectrum signal representing the Raman spectrum of the package;

detecting a Raman spectrum of an object in the package passing through the package to obtain a Raman spectrum signal representing the Raman spectrum of the object together with the package;

normalizing the Raman spectrum signal of the package and the Raman spectrum signal of the object together with the package;

determining a position of a characteristic peak of the Raman spectrum of the package, and setting an interval including the position of the characteristic peak of the Raman spectrum of the package as a calculation interval;

within the calculation interval, successively subtracting a product of the normalized Raman spectrum signal of the package and a proportionality coefficient from the normalized Raman spectrum signal of the object together with the package and successively changing the proportionality coefficient to obtain a series of package-interference-eliminated interval Raman spectrum signals;

within the calculation interval, calculating the information entropy of each of the series of package-interference-eliminated interval Raman spectrum signals and the information entropy of the Raman spectrum signal of the package;

comparing the information entropies of the series of package-interference-eliminated interval Raman spectrum signals with the information entropy of the Raman spectrum signal of the package, setting information entropies of package-interference-eliminated interval Raman spectrum signals within the calculation that are each greater than the information entropy of the Raman spectrum signal of the package into an information entropy sequence to be selected, selecting a minimum information entropy from the information entropy sequence, and selecting the proportionality coefficient corresponding to the minimum information entropy as an optimized proportionality coefficient; and subtracting a product of the normalized Raman spectrum signal of the package and the optimized proportionality coefficient from the normalized Raman spectrum signal of the object together with the package to obtain an optimized package-interference-eliminated Raman spectrum signal.

* * * * *